US012189010B2

(12) United States Patent
Blackledge et al.

(10) Patent No.: US 12,189,010 B2
(45) Date of Patent: Jan. 7, 2025

(54) DIFFUSION-WEIGHTED MAGNETIC RESONANCE IMAGING

(71) Applicant: The Institute of Cancer Research: Royal Cancer Hospital, London (GB)

(72) Inventors: Matthew Blackledge, Sutton (GB); Konstantinos Zormpas-Petridis, Sutton (GB)

(73) Assignee: The Institute of Cancer Research: Royal Cancer Hospital, London (GB)

( * ) Notice: Subject to any disclaimer, the term of this patent is extended or adjusted under 35 U.S.C. 154(b) by 340 days.

(21) Appl. No.: 17/633,849

(22) PCT Filed: Sep. 9, 2020

(86) PCT No.: PCT/EP2020/075233
§ 371 (c)(1),
(2) Date: Feb. 8, 2022

(87) PCT Pub. No.: WO2021/052838
PCT Pub. Date: Mar. 25, 2021

(65) Prior Publication Data
US 2022/0291317 A1 Sep. 15, 2022

(30) Foreign Application Priority Data
Sep. 18, 2019 (GB) .................................... 1913481

(51) Int. Cl.
*G01R 33/56* (2006.01)
*A61B 5/00* (2006.01)
(Continued)

(52) U.S. Cl.
CPC ........ *G01R 33/5608* (2013.01); *A61B 5/0033* (2013.01); *A61B 5/055* (2013.01);
(Continued)

(58) Field of Classification Search
CPC .............. G01R 33/5608; G01R 33/561; G01R 33/56341; G06T 2207/10088;
(Continued)

(56) References Cited

U.S. PATENT DOCUMENTS

2017/0108570 A1* 4/2017 Eichner ............. G01R 33/5608
2018/0356486 A1* 12/2018 Yang .................... A61B 5/0037

FOREIGN PATENT DOCUMENTS

CN 107633486 A 1/2018
WO WO 2020/198582 10/2020

OTHER PUBLICATIONS

Muckley et al., "Training a Neural Network for Gibbs and Noise Removal in Diffusion MRI," arXiv, 2019, p. 1-18. (Year: 2019).*
(Continued)

*Primary Examiner* — Siamak Harandi
*Assistant Examiner* — Daniella M. DiGuglielmo
(74) *Attorney, Agent, or Firm* — Rudy J. Ng; David Armstrong; Bozicevic, Field & Francis LLP

(57) ABSTRACT

A method of performing diffusion-weighted magnetic resonance imaging is provided. The method includes a step of: using a neural network to filter a diffusion-weighted image of an object acquired by a magnetic resonance imaging scanner, the neural network being programmed to produce an output image from the acquired image. The neural network improves the signal to noise ratio of the output image relative to the acquired image. The neural network, when applied to a synthetic knife-edge image to which Rician noise providing a signal-to-noise ratio of 13 or more is added, forms a curve of normalised values of modulation-transfer-function against frequency which has a higher area thereunder than the area under the corresponding curve of normalised values of modulation-transfer-function against frequency for a reference Gaussian smoothing filter.

11 Claims, 14 Drawing Sheets

(51) Int. Cl.
*A61B 5/055* (2006.01)
*G01R 33/561* (2006.01)
*G01R 33/563* (2006.01)
*G06N 3/08* (2023.01)

(52) U.S. Cl.
CPC .......... *A61B 5/7225* (2013.01); *A61B 5/7264* (2013.01); *A61B 5/7275* (2013.01); *G01R 33/561* (2013.01); *G01R 33/56341* (2013.01); *G06N 3/08* (2013.01); *G06T 2207/10088* (2013.01); *G06T 2207/20081* (2013.01)

(58) Field of Classification Search
CPC .......... G06T 2207/20081; A61B 5/055; A61B 5/0033; A61B 5/7225; A61B 5/7264; A61B 5/7275; G06N 3/08
See application file for complete search history.

(56) References Cited

OTHER PUBLICATIONS

Kong et al., "Noise reduction of diffusion tensor images by sparse representation and dictionary learning," BioMed Eng Online, 2016, p. 1-11. (Year: 2016).*

Garg, G. and Juneja, M., "A survey of denoising techniques for multi-parametric prostate MRI," Multimedia Tools and Applications (2019) 78: 12689-12722. (Year: 2019).*

Cheng et al., (2015) "Response evaluation in mesothelioma: Beyond RECIST" Lung Cancer 90, pp. 433-441.

Dow-Mu Koh et al., (2012) "Whole-Body Diffusion-Weighted MRI: Tips, Tricks, and Pitfalls," AJR: 199 pp. 252-262.

Eiber et al., (2011) "Whole-Body MRI Including Diffusion-Weighted Imaging (DWI) for Patients With Recurring Prostate Cancer: Technical Feasibility and Assessment of Lesion Conspicuity in DWI," Journal of Magnetic Resonance Imaging, 33: pp. 1160-1170.

Giles et al., (2014) "Whole-Body Diffusion-weighted MR Imaging for Assessment of Treatment Response in Myeloma," Radiology 271(3): pp. 785-794.

Hamstra et al., (2008) "Diffusion Magnetic Resonance Imaging: An Imaging Treatment Response Biomarker to Chemoradiotherapy in a Mouse Model of Squamous Cell Cancer of the Head and Neck," Translation Oncology, 1(4): pp. 187-194.

Hill et al., (2017) "Non-Invasive Prostate Cancer Characterization with Diffusion-Weighted MRI: Insight from In silico Studies of a Transgenic Mouse Model," Prostate Cancer Characterisation with DW-MRI, Frontiers in Oncology, 7(290) pp. 1-10.

He et al., (2015) "Delving Deep into Rectifiers: Surpassing Human-Level Performance on ImageNet Classification," Microsoft Research arXiv:1502.01852v1 [cs.CV] pp. 1-11.

Kingma and Lei Ba (2015) "Adam: A Method for Stochastic Optimization," Published as a conference paper at ICLR, arXiv:1412.6980v9 [cs.LG] 2017 pp. 1-15.

Padhani et al., (2011) "Whole-Body Diffusion-weighted MR Imaging in Cancer: Current Status and Research Directions," Radiology 261(3) pp. 700-718.

Ronneberger et al., (2015) "U-Net: Convolutional Network for Biomedical Image Segmentation," arXiv:1505.04597v1 [cs.CV] pp. 1-8.

Thoeny Md and Ross PhD (2010) "Predicting and Monitoring Cancer Treatment Response with Diffusion-Weighted MRI," Journal of Magnetic Resonance Imaging, 32 pp. 2-16.

Wang et al., (2004) "Image Quality Assessment: From Error Visibility to Structural Similarity," IEEE Transactions on Image Processing, 13(4): pp. 1-14.

Zhang et al., (2012) "A Comprehensive Evaluation of Full Reference Image Quality Assessment Algorithms," 978-1-4673-2533-2/12 IEE, ICP: pp. 1477-1480.

Zhang et al., (2018) "The Unreasonable Effectiveness of Deep Features as a Perceptual Metric," arXiv:1801.03924v2 [cs.CV] pp. 1-14.

Zhao et al., (2018) "Loss Function for Image Restoration with Neural Network," arXiv:1511.08861v3 [cs.CV] pp. 1-11.

Zu et al., (2018) "Image reconstruction by domain-transform manifold learning," Nature, 555: pp. 487-501.

Zhu et al., (2018) "Deep learning MR reconstruction with Automated Transform by Manifold Approximation (AUTOMAP) in real-world acquisitions with imperfect training" Proc. Intl. Soc. Mag. Reason. Med. 0572: pp. 1-3.

Muckley et al., (2019) "Training a Neural Network for Gibbs and Noise Removal in Diffusion MRI." Magnetic resonance in medicine, vol. 85, No. 1, pp. 413-428.

Patch-Based Techniques in Medical Imaging, 4th International Workshop, Sep. 20, 2018, Granada, Spain, IET, Manjon et al., MRI Denoising Using Deep Learning, pp. 12-19.

Thakur et al., (2019), "State-of-are analysis of image denoising methods using convolutional neural networks." IET Image Processing, vol. 13, Issue 13, pp. 2367-2380.

Kong et al., (2016) "Noise Reduction of Diffusion Tensor Images by Sparse Representation and Dictionary Learning", Biomedical Engineering Online, 15:5:11 pages.

Garg and Juneja (2019) "A survey of denoising techniques for multi-parametric prostate MRI," Multimedia Tools and Applications 78: 12689-12722.

* cited by examiner

DIFFUSION-WEIGHTED MAGNETIC RESONANCE IMAGING

FIELD OF THE DISCLOSURE

The present disclosure relates to performance of diffusion-weighted magnetic resonance imaging.

BACKGROUND

Whole-body diffusion-weighted MR-imaging (WBDWI) is an attractive non-invasive tool for staging and response evaluation of lymphoma and metastatic bone disease from prostate [1], [2] and breast [3] cancers; WBDWI has recently been incorporated into NICE guidelines for assessing disease extent of evaluation of myeloma-related bone disease [4]. This technique sensitizes MR-imaging contrast to the diffusion rate of water within tissues through application of magnetic gradients, which can be manipulated to adjust the magnitude of diffusion-weighting within images. The contrast generated between diseased and healthy tissues using this technique provides radiologists with a sensitive tool for reviewing the extent of bony disease within the skeleton. The degree of diffusion weighting within an image can be manipulated at will through modification of the so-called 'b-value', which encapsulates the timing and strengths of the diffusion-weighting gradients into a single variable (typically in the range 0-5000 s/mm² on clinical systems). By acquiring images for the same anatomical location at two or more b-values, WBDWI offers voxel-wise quantification of the 'apparent diffusion coefficient' (ADC) of water, a potent surrogate marker of tumour response to anti-tumour treatments. Previous histopathological studies have demonstrated that an increase in ADC following treatment can represent a disruption of the tumour microenvironment, and eventually a reduction in tumour cellularity to indicate tumour necrosis [5]—[7].

Modern WBDWI studies are typically acquired in the axial plane through a series of sequential imaging stations from head to mid-thigh, with each station consisting of 30-50 imaging slices. In addition to this, (i) b-values are applied in three or more directions to derive directionally independent measurements of ADC, and (ii) as the technique has low signal-to-noise ratio (SNR) compared to anatomical MR-imaging, each diffusion-weighted image is acquired multiple times (the average provides an image with higher SNR). This can lead to 30-50 image acquisitions per slice (when using 3 b-values), requiring 20-30 minutes total acquisition time. With the addition of anatomical imaging sequences and patient set-up and positioning, this requires a total study time of approximately 1 hour. This provides a calamitous bottleneck for the adoption of WBDWI into a general clinical workflow; an ever-increasing patient population increases capacity pressures on imaging centres, which are then less willing to perform such long imaging studies. Furthermore, patients for which WBDWI has shown to be clinically useful are typically frail and have painful bony conditions, which lowers patient acceptance of the methodology. Accelerated WBDWI acquisition schemes are highly sought after.

SUMMARY

In general terms the present disclosure provides the use of a neural network to filter a diffusion-weighted image of an object acquired by a magnetic resonance imaging scanner, the neural network being programmed to produce an output image from the acquired image. Surprisingly, a neural network used in this way can provide 'clinical-grade' images from subsampled data, potentially reducing acquisition times by a significant amount.

More particularly, in a first aspect, the present disclosure provides a method of performing diffusion-weighted magnetic resonance imaging, the method including a step of:

using a neural network to filter a diffusion-weighted image of an object acquired by a magnetic resonance imaging scanner, the neural network being programmed to produce an output image from the acquired image;

wherein the neural network improves the signal to noise ratio of the output image relative to the acquired image; and wherein the neural network, when applied to a synthetic knife-edge image to which Rician noise providing a signal-to-noise ratio of 13 or more (preferably 5 or more, and more preferably 3 or more) is added, forms a curve of normalised values of modulation-transfer-function against frequency which has a higher area thereunder than the area under the corresponding curve of normalised values of modulation-transfer-function against frequency for a reference Gaussian smoothing filter, $\tilde{G}$:

$$\tilde{G}\{f(x, y)\} = \frac{1}{\sqrt{2\pi\sigma^2}} \exp\left\{-\frac{(x^2 + y^2)}{2\sigma^2}\right\} \circledast f(x, y) \rightarrow g(x, y)$$

where $f(x, y)$ is the noisy synthetic knife-edge image, $g(x, y)$ is the filtered image, $\circledast$ is the convolution parameter, and $\sigma^2$ is the smoothing variance set such that $\sigma^2=4$.

Advantageously, the neural network can be used to improve image quality of single-acquisition DWI images. Thus the acquired image may be acquired by the magnetic resonance imaging scanner at a given b-value and a given orientation for that b-value and without signal averaging.

The neural network may be a spatially variant filter. Thus the degree of smoothing performed by the network within a certain region of the acquired image can be dependent on the position of that region within the entire imaging field. Particularly in the context of an object that is a human or animal subject, this allows the network to learn anatomical position in order to tune the degree of smoothing it performs at a particular anatomical location.

The neural network may be a convolutional neural network.

The method may include a preliminary step of: acquiring the diffusion-weighted image using the magnetic resonance imaging scanner.

The acquired image may be acquired at a first b-value and at given location in the object. In this case, the method may include a further step of: combining the output image with one or more further diffusion-weighted images acquired (e.g. by repeating the acquiring and using steps for each of the further images) at the given location in the object but at respective different b-values to derive an image of an apparent diffusion coefficient of water at the given location in the object.

The object may be a human or animal subject. In this case, the method may include a further step of: analysing the output image or an image derived therefrom for assessment of disease extent (e.g. cancer extent) in the human or animal subject.

The method is typically computer-implemented. Accordingly, further aspects of the present disclosure provide: a computer program comprising code which, when the code is executed on a computer, causes the computer to perform the method of the first aspect; a computer readable medium storing a computer program comprising code which, when the code is executed on a computer, causes the computer to perform the method of the first aspect; and a computer system programmed to perform the method of the first aspect. For example, a further aspect of the present disclosure provides an imaging system for performing diffusion-weighted magnetic resonance imaging, the system including:

a magnetic resonance imaging scanner for acquiring a diffusion-weighted image of an object; and
a computer system which receives the acquired image, and is programmed with a neural network which filters the acquired image to produce an output image from the acquired image;
wherein the neural network improves the signal to noise ratio of the output image relative to the acquired image by a factor of X as measured by Y; and
wherein the neural network, when applied to a synthetic knife-edge image to which Rician noise providing a signal-to-noise ratio of 13 or more (preferably 5 or more, and more preferably 3 or more) is added, forms a curve of normalised values of modulation-transfer-function against frequency which has a higher area thereunder than the area under the corresponding curve of normalised values of modulation-transfer-function against frequency for a reference Gaussian smoothing filter, $\tilde{G}$:

$$\tilde{G}\{f(x, y)\} = \frac{1}{\sqrt{2\pi\sigma^2}} \exp\left\{-\frac{(x^2 + y^2)}{2\sigma^2}\right\} \circledast f(x, y) \to g(x, y)$$

where f(x, y) is the noisy synthetic knife-edge image, g(x, y) is the filtered image, $\circledast$ is the convolution parameter, and $\sigma^2$ is the smoothing variance set such that $\sigma^2=4$. The network may be a spatially variant filter. The network may be a convolutional neural network.

In another aspect, the present disclosure provides a method of training a neural network programmed to produce an output image by filtering a diffusion-weighted image of an object acquired by a magnetic resonance imaging scanner, the method including:

providing a training set of diffusion-weighted images of one or more objects acquired by one or more magnetic resonance imaging scanners, each image of the training set having been acquired by a respective magnetic resonance imaging scanner at a respective location in the body, at a respective b-value and a respective orientation for that b-value, and without signal averaging, wherein for each location, images are provided at different b-values and different orientations for each b-value, and wherein plural images are provided for each combination of a given location, a given b-value and a given b-value orientation;
combining the plural images from the training set for each combination of a given location, a given b-value and a given b-value orientation to form a respective ground truth image for the given location and the given b-value; and
training the neural network to minimise a cost function that measures similarity between each image of the training set and the corresponding ground truth image for the same location and the same b-value as that image.

Thus the method of this other aspect may be used to train the network of the first aspect.

Conveniently, the cost function may measure similarity using a mean-absolute-error. The neural network may be a convolutional neural network. The training set of diffusion-weighted images may be images of human or animal subjects.

The term "computer readable medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to, portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer readable medium. One or more processors may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

BRIEF DESCRIPTION OF THE DRAWINGS

Embodiments of the present disclosure will now be described by way of example with reference to the accompanying drawings.

DETAILED DESCRIPTION

In the following we describe a study exploring innovative uses of Artificial Intelligence (AI) to drastically reduce scan times in WBDWI and thus render it a feasible clinical approach for diagnosing, staging, and assessing treatment response of diseases such as lymphoma and metastatic bone disease from prostate and breast cancers. In brief, the approach effectively recovers fully sampled WBDWI images from a heavily under-sampled diffusion-weighted image (e.g. single b-value direction and no multiple averages), cutting acquisition times in the order of 5-10 fold. To train the AI model we use a prospective WBDWI imaging protocol, which may be acquired on most clinical scanners. We validate our technique through a second prospective cohort of patients with metastatic prostate cancer and myeloma-related bone disease. In addition, we demonstrate the feasibility of the technique for diffusion-weighted imaging acquired over a smaller field of view through retrospective analysis of a cohort of patients with malignant pleural mesothelioma (MPM) [8]. Our methodology provides an image-processing pipeline that could be easily implemented on most WBDWI post-processing systems.

Materials and Methods

Patient Population

All studies were performed in accordance with the Declaration of Helsinki, and ethical approval was obtained for these patient cohorts.

Training WBDWI Cohort

Figure 1:
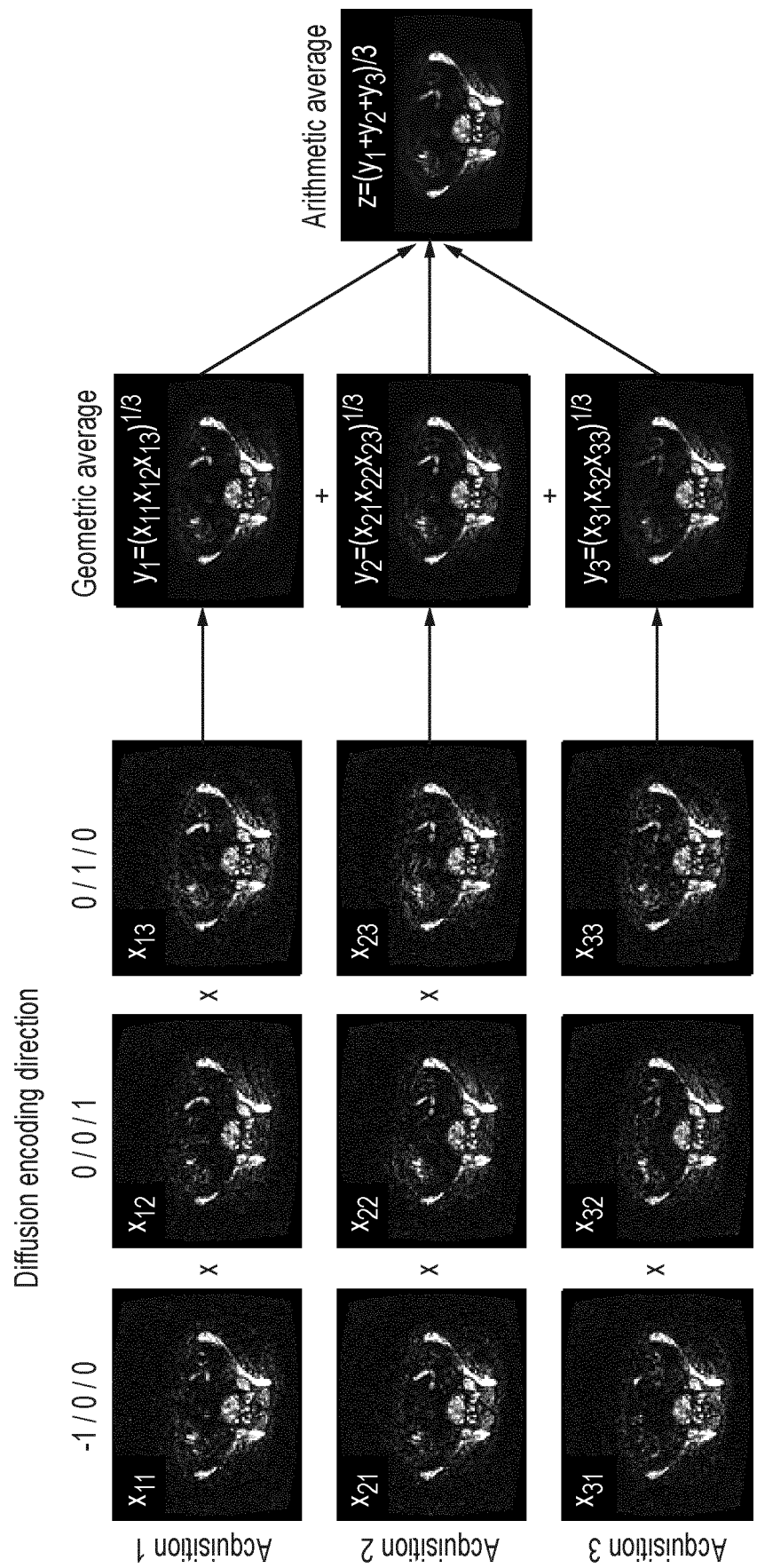
FIG. 1: Generation of 'clinical-standard' images, z, from the single acquisition images, $x_{ij}$, was achieved by (i) computing the geometric average over the different directions, j, and computing the arithmetic average over the resulting trace-weighted images, $y_i$. Such operations mimic the processing performed by most clinical scanners when acquiring WBDWI. In clinical scanners only the averaged images (z) are retained, whilst all other data is removed to reduce storage requirements.

WBDWI was acquired in 17 patients with suspected metastatic prostate cancer in the skeleton on a 1.5T MR system (Siemens Aera, Erlangen, Germany). Axial, spin-echo, echo-planar imaging (SE-EPI) was acquired from skull-base to mid-thigh using a slice thickness of 5 mm, inversion-time (TI) 180 ms (for fat-signal suppression), echo-time (TE) 79 ms, repetition-time (TR) 12.7 s, field-of-view (FoV) 128×104 pixels (interpolated to 256×208), resolution 1.68×1.68 mm$^2$ (following interpolation), pixel readout bandwidth (BW) 1955 Hz/pixel, and GRAPPA parallel imaging with acceleration factor R=2. Images at each axial location were acquired using b-value of 50, 600 and 900 s/mm$^2$; for each b-value we acquired an image using each of the orthogonal orientations $(b_x, b_y, b_x) \propto (-1, 0, 0)$, $(0, 1, 0)$, and $(0, 0, 1)$. A single image was acquired for each b-value/orientation pair (i.e. no signal averaging was applied), and a 'trace-weighted' image computed as the geometric average of these images in post-processing (see FIG. 1 for an illustrative exposition of this process). These acquisitions were repeated three times, and the arithmetic average of the three subsequent trace-weighted images provided the conventional clinical WBDWI image as a 'gold-standard', as shown in FIG. 1 (number of signal averages, NSA=3). All images (individual acquisitions and the resultant final averaged image) were stored for further processing. These data were split into a training/validation cohort as 14/3 patients respectively.

Test WBDWI Cohort

WBDWI was prospectively acquired in a cohort of 24 patients with metastatic prostate cancer (N=19), metastatic breast cancer (N=2), and multiple myeloma (N=3) on the same scanner as for the training cohort. For each patient, we acquired data using two WBDWI protocols within the same study (the patient remained on the couch between studies). Firstly, the same protocol as for the training cohort, but only obtaining a single average (NSA=1) and single b-value direction, $(b_x, b_y, b_x) \propto (0, 0, 1)$. Secondly, we performed a conventional clinical WBDWI scan with the following parameters: slice thickness=5 mm, TI=180 ms, TE=64 ms, TR=6.2 s, FoV=134×108 pixels (interpolated to 268×216), resolution=1.6×1.6 mm² (following interpolation), BW=2330 Hz/pixel, R=2 (GRAPPA), with NSA=4; data were acquired for b-values 50, 600, and 900 s/mm² over three orthogonal diffusion-encoding directions to obtain trace-weighted images. We attempted to match the field of-view for both protocols from either skull base (prostate cancer) or skull vertex (myeloma) to mid-thigh in both protocols. In post-processing, the clinical protocol was resampled to match the field-of-view and resolution of the data acquired with shorter single acquisition protocol. Approximate acquisition times for these protocols were ~5 minutes for the single acquisition protocol and ~22-25 minutes for the clinical protocol.

Lung Cohort

To demonstrate that our approach was successful in other diffusion-weighted imaging (DWI) studies, we retrospectively evaluated data from a cohort of patients evaluated for presence of malignant pleural mesothelioma (MPM). This cohort consisted of 28 patients scanned using DWI to assess response of MPM to a targeted agent; only baseline scans were used for evaluation in this study. Imaging consisted of a similar protocol to the whole-body training cohort, using a 1.5T scanner (Siemens Avanto, Erlangen, Germany): images were acquired axially using SE-EPI with b-values=100, 500 and 800 s/mm² over three orthogonal directions $(b_x, b_y, b_x) \propto (-1, 0, 0), (0, 1, 0)$, and $(0, 0, 1)$. For each b-value/direction pair, acquisition was repeated four times to obtain a clinical-grade scan from the geometric and arithmetic averages of the different directions and repetitions respectfully (as per FIG. 1). Images were acquired over two imaging stations (30 slices/station) to cover the whole chest, with SPAIR fat suppression, TE=92 ms, TR=6 s, FoV=128× 92, resolution=3×3 mm², BW=1860 Hz/pixel, and R=2 (GRAPPA). These data were split into a training/validation cohort as 20/8 patients respectively.

AI Network Architecture

Figure 2:
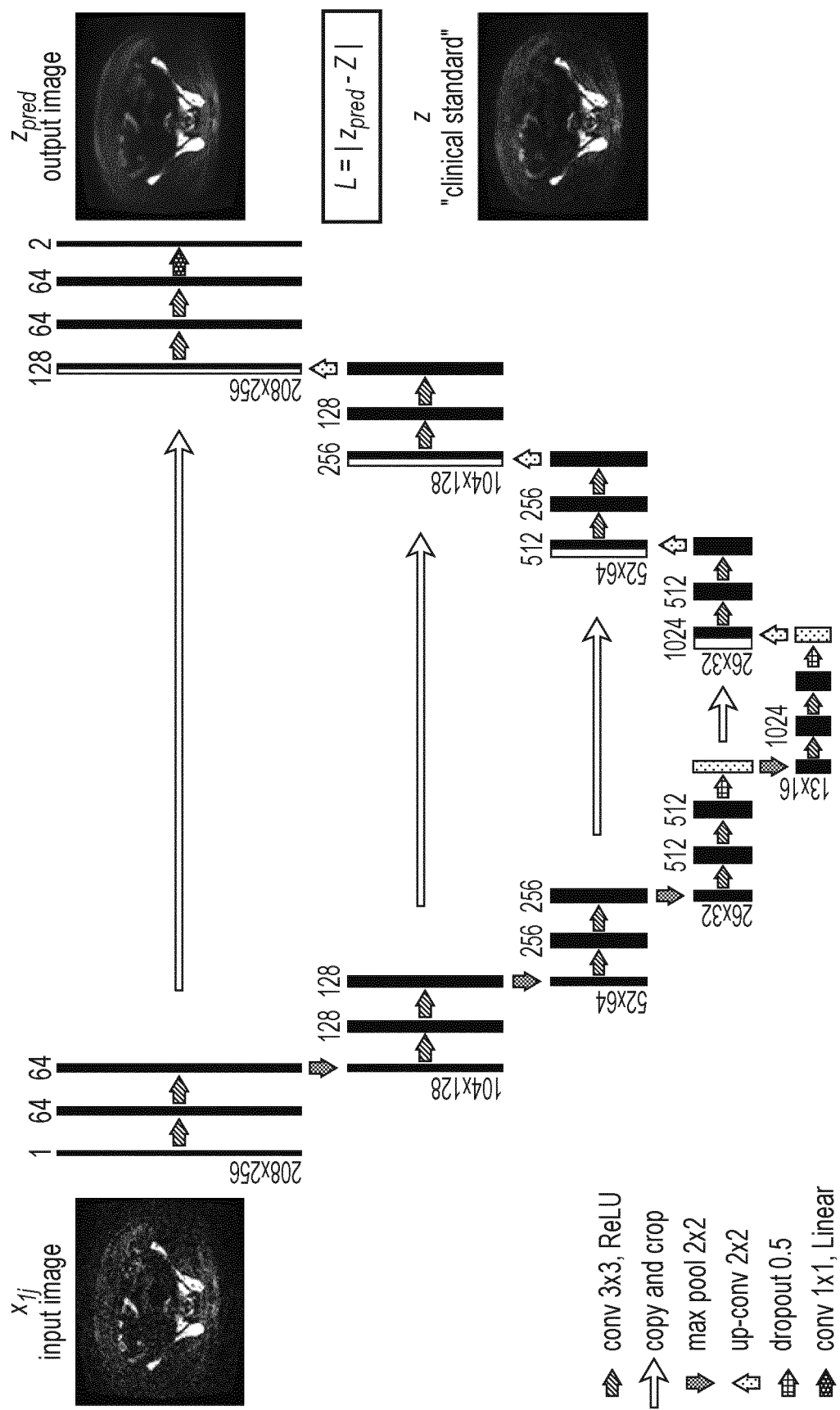
FIG. 2: An illustration of our U-NET-like architecture for processing input noisy images from a single acquisition at a random direction, $x_{1j}$, to predict image $z_{pred}$. The mean-absolute error (L) is used as the cost function to evaluate the perceived closeness of a predicted image to the acquired clinical-standard/ground-truth image, z.

Our deep-learned de-noising image filter (DNIF) comprises a convolutional neural network based on the U-Net architecture [9] as illustrated in FIG. 2. An image of size 256×208 pixels is provided as input into the network (post-interpolation image size of the training WBDWI cohort data), and normalised from range 0-4095 to range 0-1. A linear activation was utilised for the last layer, whilst a ReLU activation function was used in all preceding layers. We constrained the weights incident to each hidden unit to have a norm value less or equal to 3; the weights of the layers were randomly initialized using He normal initialization [10], and the network was optimized using Adam [11] with a learning rate=$10^{-3}$.

To train the network we minimised a cost function that measures the similarity between the DNIF-filtered image derived from noisy input image (NSA=1) with that of the 'ground truth' clinical image after averaging (NSA=9). The default choice would be to minimise the mean-squared-error (MSE) between the two images. However, due to the metric's well-known limitations in assessing image quality as perceived by a human observer [12], we used two different image similarity metrics, which better correlate with human perception of image quality: (i) the mean-absolute-error (MAE), and (ii) a combination of the mean-absolute-error and the structural similarity (SSIM) index [13] (Equation 1).

$$L^{mae/SSIM} = a \cdot L^{mae} + (1-a) \cdot L^{SSIM} \quad \text{(Equation 1)}$$

here a is the weight of the contribution for each error metric to the function. After testing different values, we empirically set a to 0.7 (we observed that small variations of a did not significantly affect the results).

The network was trained on the 59400 WBDWI slices from the first 14 patients in the training WBDWI cohort (~14 patients×3 directions×3 acquisitions×3 b-values×150 slices), using a batch size of 36 images for 15 epochs. Its performance was validated on the independent validation set consisting of 15120 images from the 3 remaining patients. The trained network was subsequently applied to the single acquisition data acquired in the test WBDWI cohort.

For the lung cohort, we retrained the network (network weights randomly initialised) on 43200 WBDWI slices from the first 20 patients, and tested it using an independent test set of 15120 MRI slices from the remaining 8 patients. We used linear interpolation to resize the images such that the input image size was 256×208 pixels, which were then normalised from range 0-939 to range 0-1 prior to input into the model. For comparison, we also applied the network trained from the training WBDWI cohort to the same set of test lung patients.

Data Analysis

Training WBDWI Cohort

An expert radiologist (>10 years' experience) blindly scored images from the three test patients within this cohort for (i) SNR, (ii) contrast-to-noise ratio (CNR), (iii) tumour detection, (iv) presence of image artefacts, and (v) overall image quality using a Likert scale: 1=poor to 5=excellent. Diffusion-weighted images at b=900 s/mm² and ADC maps resulting from each of the NSA=1, NSA=9, and DNIF methods were used for this visual assessment. In addition, for the test patients a radiologist outlined regions of bone disease on the averaged data using an in-house semi-automatic segmentation tool for metastatic disease identified with WBDWI studies. These regions of interest (ROIs) were copied onto ADC maps calculated from (i) the single acquisition images (NSA=1), (ii) the 'clinical-standard' images after averaging (NSA=9), and (iii) the DNIF-filtered images resulting from application of the network to the NSA=1 data. The mean ADC of bone disease within these regions was compared.

Test WBDWI and Lung Cohorts

The quality of DNIF filtered images at b=900 s/mm² was visually compared to the clinical standard for all patients in the test WBDWI cohort, along with the resultant ADC maps calculated using DNIF-filtered b=50, 600, and 900 s/mm² images. A similar visual comparison was made for the 8 test patients from the lung patient cohort, comparing the DNIF-filtered b=800 s/mm² with the averaged clinical standard and the ADC maps calculated using the b=100, 500, and 800 s/mm² images Results AI Network Architecture Within 15 epochs, the network minimized the mean-absolute-error from $0.87 \times 10^{-3}$ to $0.53 \times 10^{-3}$ and the MAE/SSIM error from $0.39 \times 10^{-2}$ to $0.11 \times 10^{-2}$. Both cost functions result in the same MAE solution ($0.53 \times 10^{-3}$). Interestingly, using either the $L^{mae}$ or $L^{mae/SSIM}$ cost functions, the network reached a better solution for the mean-squared-error than trying to minimize the mean-squared-error directly (MSE from $L^{mae}$: $1.89 \times 10^{-6}$ vs MSE from $L^{mae/SSIM}$: $1.88 \times 10^{-6}$ vs $L^{MSE}$: $2.7 \times 10^{-6}$). Visual inspection by an expert radiologist concluded that the network trained on the $L^{mse}$ cost function applied too much smoothing on the images without preserving the edges well. This metric was not used for further analysis.

The network required 8 hours of training on the WBDWI data using a Tesla P100-PCIE-16 GB GPU card. In terms of computational efficiency, the trained network needs only ~1 s to process a single low-SNR image on a MacBook Pro (3.5 GHz, Intel Core i7 CPU).

Training WBDWI Cohort

Figure 3:
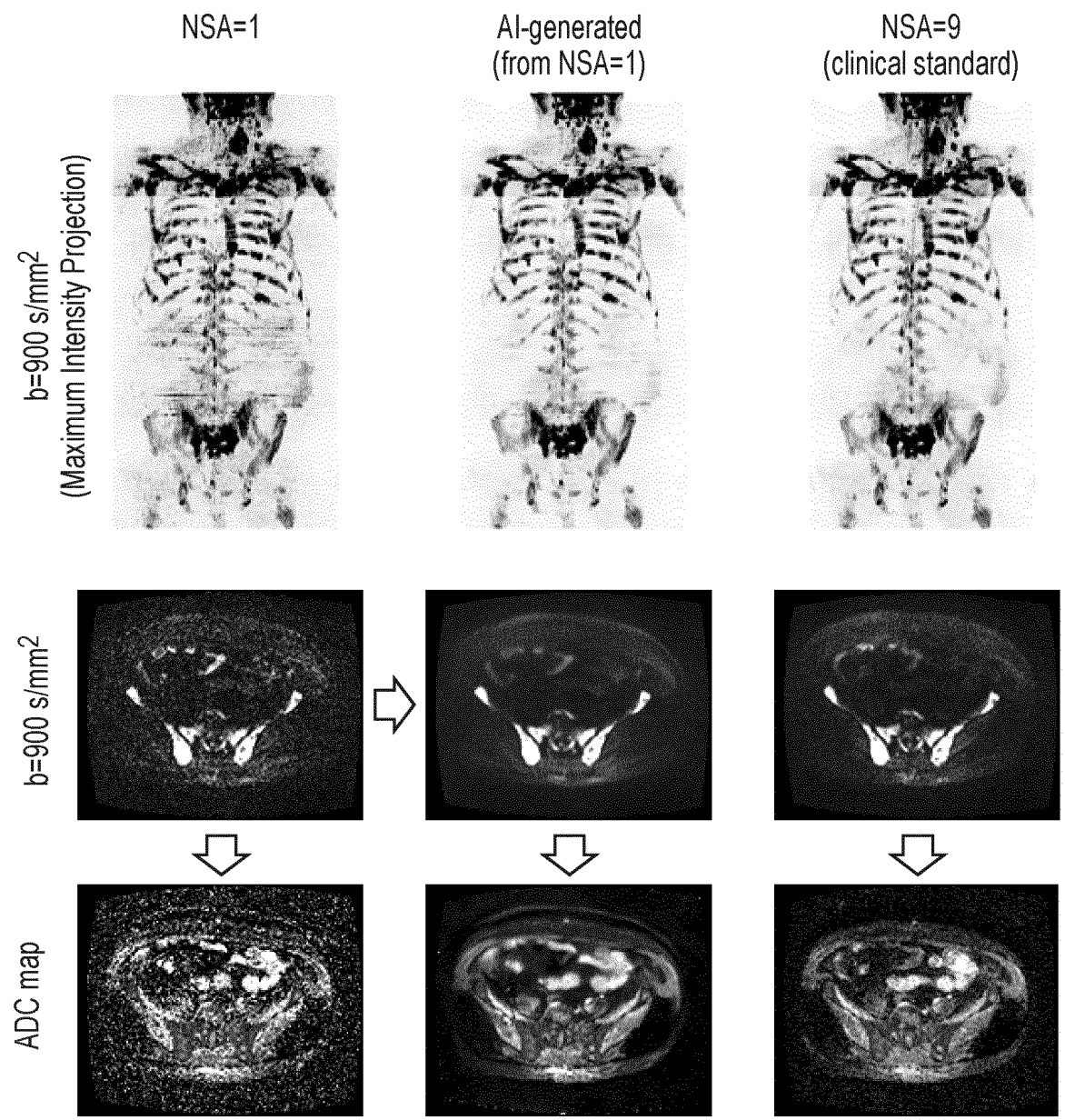
FIG. 3: An example test-patient dataset from the training WBDWI cohort. Following application of the De-Noising Image Filter (DNIF) filter (centre column), image quality in b=900 s/mm² is improved over the inherently noisy single acquisition images (left column), with equivalent image quality to the clinical standard (right column). This is clear both on axial images (middle row), and on resulting coronal maximum intensity projections (top row) at the same b-value. In addition, image quality in ADC maps is greatly improved (bottom row), with equivalent quantification to the clinical standard ADC map.

An example of the DNIF filter applied to the entire field of view in one of the test patients is illustrated in FIG. 3. It is clear that the DNIF filter is able to successfully reduce the influence of imaging noise in the input NSA=1 image. This noise reduction leads to superior image quality in resulting calculated ADC maps. DNIF-filtered images radiologically outperformed NSA=1 and NSA=9 images in all three test patients (average Likert score across all 5 criteria 3.73 [3.6-4.0] vs 1.6 [1.2-1.8] and 2.53 [2.4-2.6] respectively), thus improving image quality.

Figure 4:
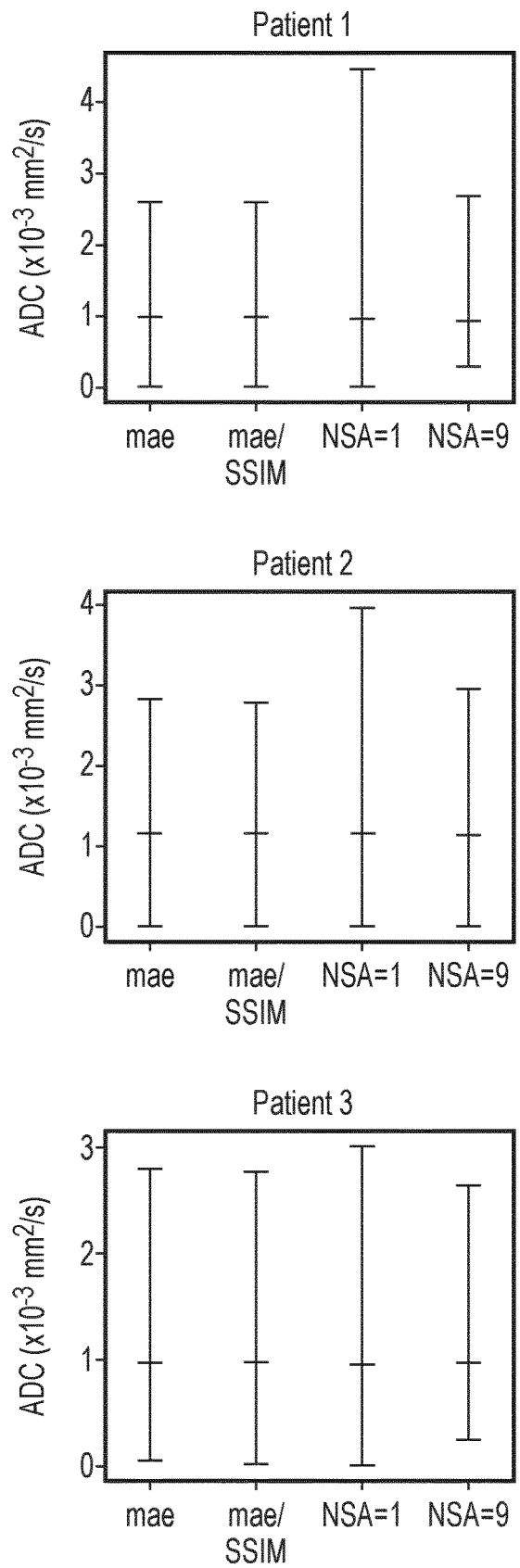
FIG. 4: Violin plots of the ADC distributions within segmented bone disease for the three test patients in the training WBDWI cohort. Only positive ADC values were included. There is a reduction in the range of ADC values for the deep-learned DNIF networks trained with the MAE and MAE/SSIM cost functions respectively. We attribute this to an improvement in the SNR of the derived ADC maps following DNIF smoothing.

Mean ADC values measured within bone disease from AI-generated images deviated from mean disease ADC calculated from NSA=9 images by an average of 2.4% [range: 0.6-4.5] (within previously reported repeatability limits for mean ADC measurements). Violin-plots of ADC values within segmented regions are illustrated in FIG. 4, which demonstrates the ability of DNIF to reduce the range of calculated ADC measurements as a result of reducing the SNR in calculated ADC maps. As little difference was observed between the performance of MAE and MAE/SSIM cost-functions, we chose to use the MAE-derived networks for further evaluation due to the simplicity of the cost-function and that fact that no weighting parameter 'a' is required in its definition (Equation 1).

Test WBDWI and Lung Cohorts

Figure 5:
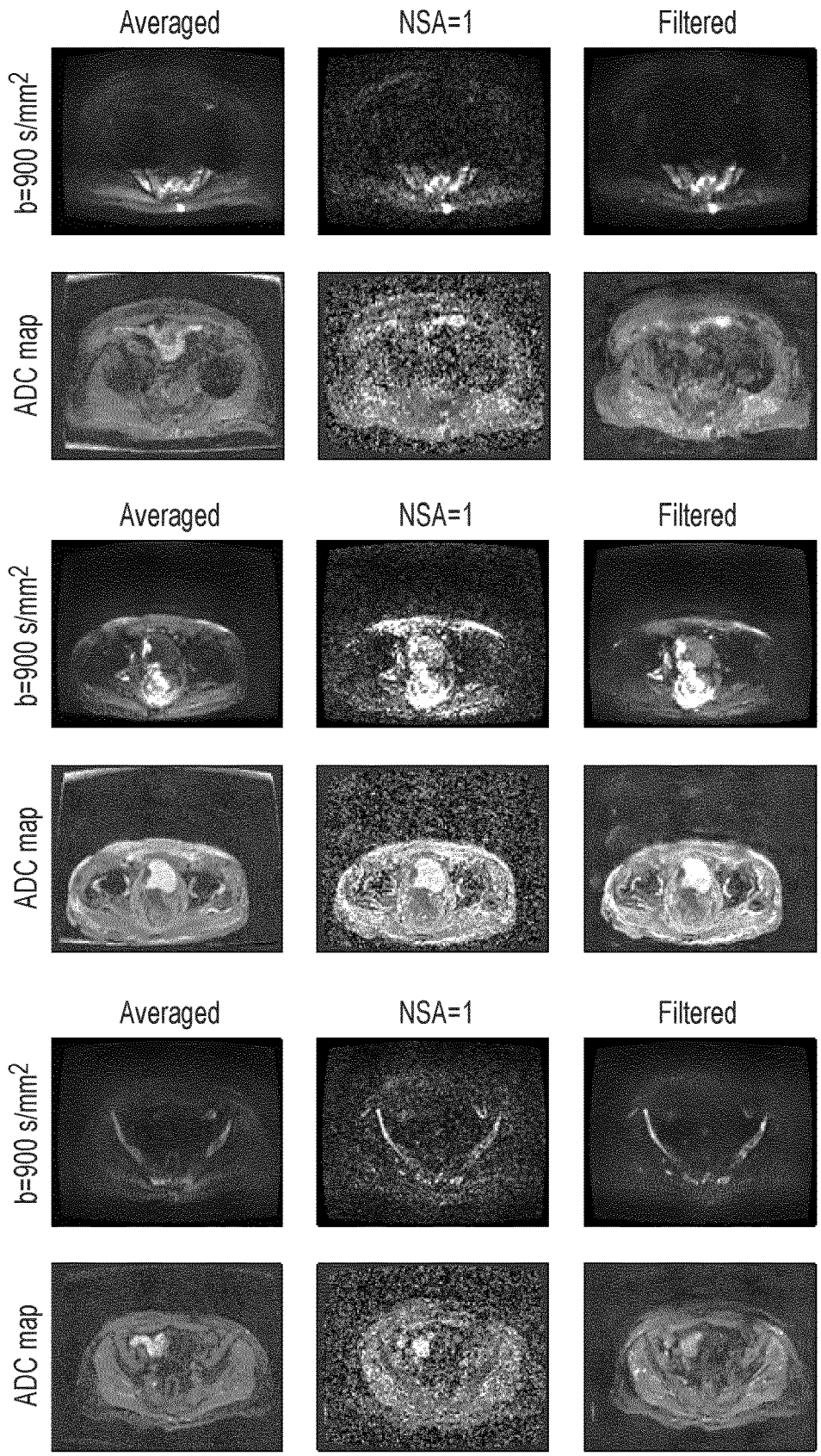
FIG. 5: Example axial b=900 s/mm$^2$ images and ADC maps for the clinical standard, unfiltered single acquisitions (NSA=1), and DNIF-filtered images for size of the patients in the test WBDWI cohort. A clear improvement in image and map quality is observed in all cases when using the DNIF filter over the unfiltered NSA=1 image.
Figure 5:
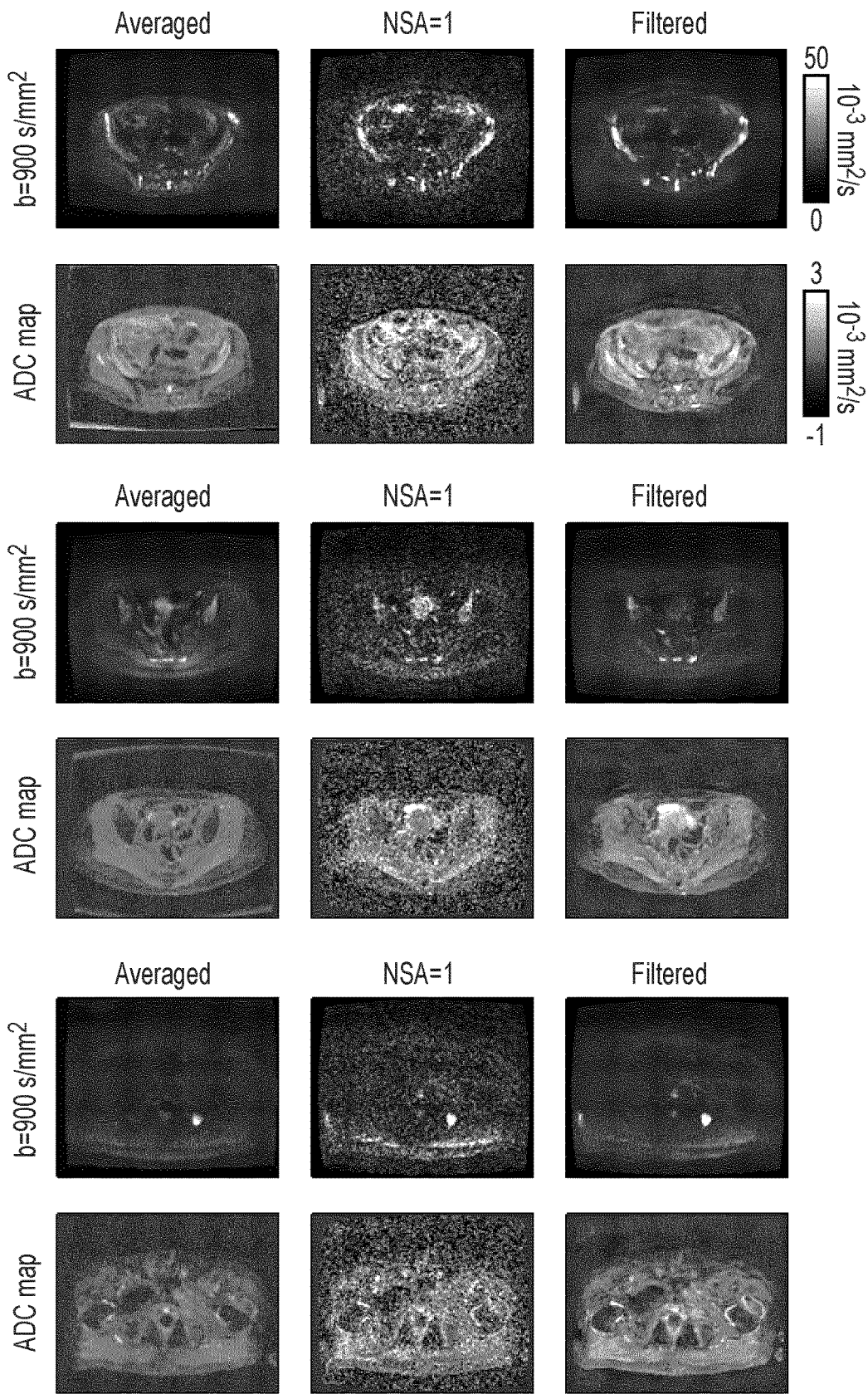

Application of the DNIF filter was successful in all 22 test patients within the test WBDWI cohort. Improvements in image quality in terms of contrast to noise ratio for high b-value images and resulting ADC maps was observed for all patients; results for six randomly selected patients are illustrated in FIG. 5.

Figure 6:
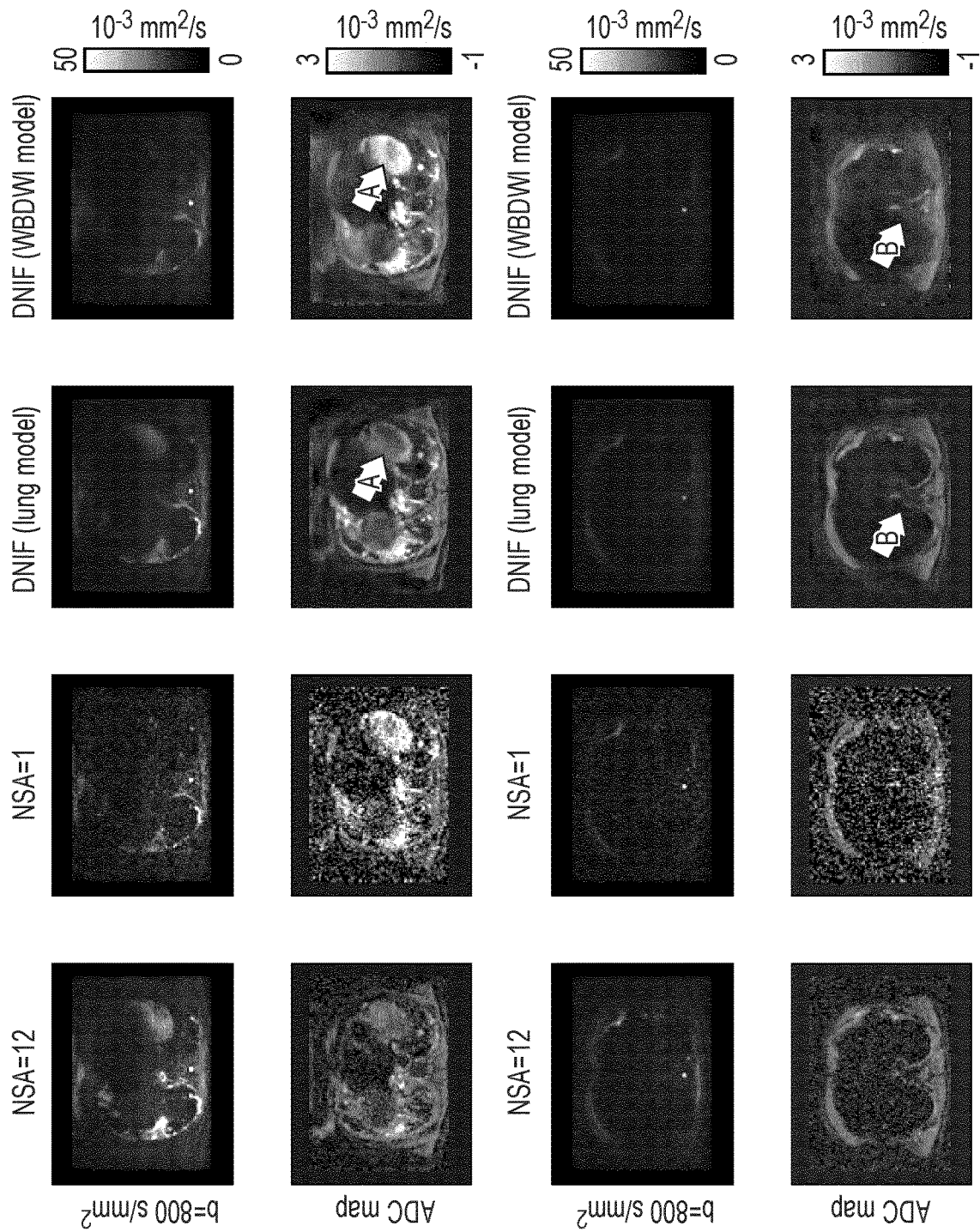
FIG. 6: Three patient examples datasets from the test arm of the lung cohort. Although a clear improvement in image quality is observed for filtered using the DNIF pre-trained using the WBDWI images, a further improvement is seen when re-training the filter using data acquired specifically in patients with MPM. In particular, this improvement is observed with respect to crisper disease contrast in high b-value images (arrows A), sharper tissue boundaries (arrows B), and more accurate ADC measurements (arrows C).
Figure 6:
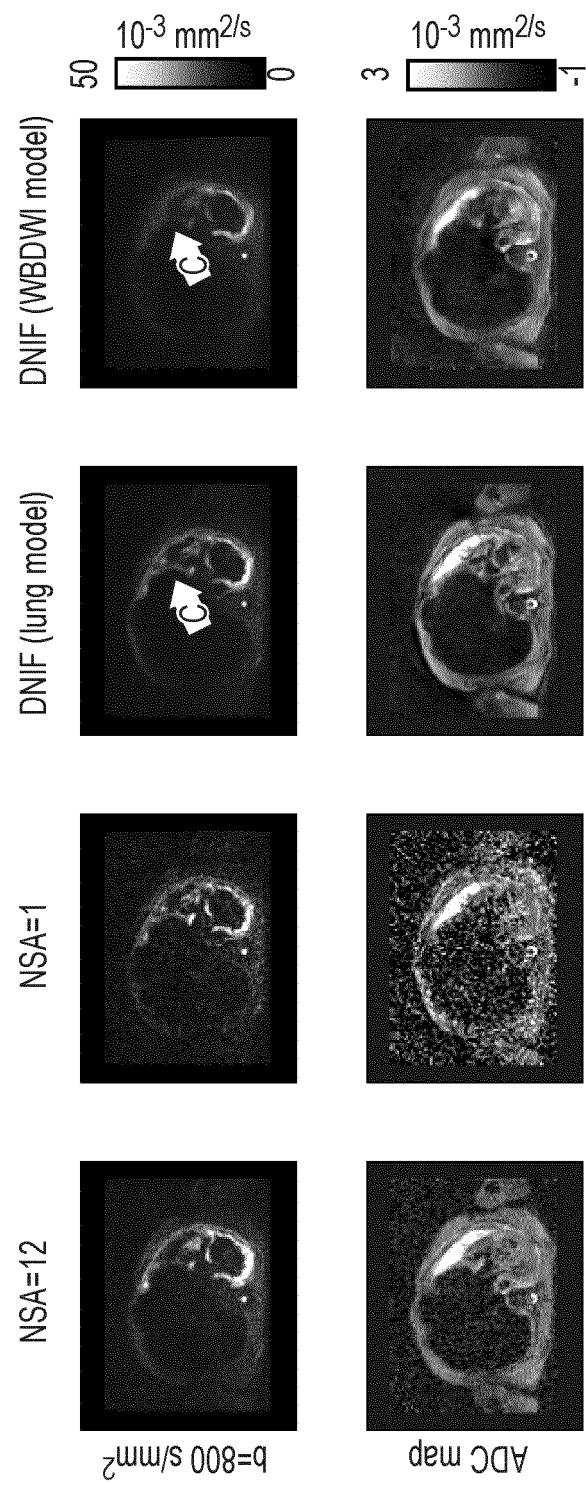

FIG. 6 compares results for three of the test patient datasets from the lung cohort, demonstrating NSA=1 images filtered with networks trained using the original training WBDWI cohort, and another network re-trained using the new lung data. Results indicate that whilst the WBDWI trained network may still be useful for smoothing DW-images acquired in MPM, the architecture can certainly be improved by re-training with disease-specific data.

Discussion

The architecture of our WBDWI deep-learned de-noising image filter (DNIF) dramatically improves image quality in heavily subsampled WBDWI acquisitions. We have tested our trained algorithm on a prospectively collected dataset of WBDWI images acquired in patients with either metastatic prostate cancer or myeloma-related bone disease, and compared DNIF-filtered images with 'clinical standard' WBDWI image acquired during the same imaging study. Our results indicate that the DNIF is able to provide 'clinical-grade' WBDWI images from subsampled data, potentially reducing acquisition times by a significant amount (~25 minutes to ~5 minutes in our prospective study). Such time savings could reduce scanning costs, rendering WBI appropriate for screening studies and sparing patient time and/or discomfort. We have provided evidence that ADC measurements made using DNIF filtered images provide equivalent information to measurements made using fully sampled WBDWI data, indicating that estimates of mean ADC within bone disease calculated using DNIF may be sufficiently robust for monitoring treatment response. Our approach for acquiring the training data needed for deriving the DNIF network can be adopted and applied at any imaging centre using existing MR hardware. We have demonstrated that our proposed methodology can be adapted to other disease types investigated with DWI, such as malignant pleural mesothelioma, that typically use a smaller field-of-view than used for total body measurements. Moreover, we have demonstrated that although the WBDWI-trained DNIF filter can be used to improve image quality of single-acquisition DWI images acquired in MPM, the technique is improved if training data is acquired for the disease in question. More generally, the network would benefit from the addition of training data from other institutions, MR vendors, and different protocols, in order to develop a filter that is robust enough to evaluate data from any WBDWI study.

Using our described protocol for acquiring individual WBDWI acquisitions and obtaining clinical-standard WBDWI scans through post-processing, we expect that the network can be trained for clinical protocols on different scanners. Such an approach can exploit the concept of 'transfer-learning'; by using the weights from our DNIF network as an initialisation, an individual site may not need to acquire much more data to train a robust network specific to that site.

The training of the DNIF neural network is based on trying to make the input image as similar to the "ground truth" as possible. However, the correct assessment of image similarity by algorithms is an ongoing problem in the computer vision field. The default choice, the mean-squared-error, is predominantly used due to its simplicity and well-understood properties, but suffers from many known limitations, including strong assumptions; this metric assumes that noise is white (Gaussian distributed) and not dependent on local image characteristics [14]. Furthermore, this metric, although valid for other applications, produces images that do not correlate well with human perception of image quality (two images with very low mean-squared-error can look quite different to a human observer) [12]. In the healthcare domain, this can pose a major problem since radiologists have to make clinical decisions based on the resulting images. In this study, we investigated another local metric, the mean-absolute-error and we, also, combined it with a metric closer to human perception, the SSIM.

The similarity metrics such as MSE, MAE, and SSIM show that the input image, despite its poor visual quality and low SNR, is numerically similar to the "ground-truth" image. This does not leave much room for the network to minimize the error-metric further. Nonetheless we have achieved low MSE by minimising the MAE, even though these metrics have different convergence properties. In particular, MAE does not over-penalise large errors. This also agrees with findings of Zhao et al, where they attempt joint de-noising and de-mosaicking on an image restoration problem [14].

Understanding the inner workings of any deep-learning algorithm can be a difficult task. However, evidence of how deep-learning networks arrive at a particular result is useful if such technologies are to be embraced within the healthcare sector, and to support application for medical regulatory approval. In the Appendix, we provide evidence for how our DNIF filter may be working. We also provide preliminary evidence that the DNIF filter, in the least, is (i) non-linear, (ii) spatially variant, (iii) non-local, and (iv) edge-preserving. This demonstrates an advantage of the deep-learning approach, as generating 'hand-crafted' filters that can simultaneously achieve these properties is generally impractical. We posit from these results that the DNIF filter is learning complex relationships between pixels within the field-of-view based on their relative position and relative intensity. Moreover, we believe (due to spatial variance in particular) that the DNIF filter is learning anatomical position in order to tune the degree of smoothing it performs at a particular anatomical location.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

REFERENCES

All references referred to herein are hereby incorporated by reference.
  [1] D. M. Koh et al., "Whole-body diffusion-weighted mri: Tips, tricks, and pitfalls," *American Journal of Roentgenology*, vol. 199, no. 2. pp. 252-262, 2012.
  [2] M. Eiber et al., "Whole-body MRI including diffusion-weighted imaging (DWI) for patients with recurring prostate cancer: Technical feasibility and assessment of lesion conspicuity in DWI," *J. Magn. Reson. Imaging*, vol. 33, no. 5, pp. 1160-1170, 2011.
  [3] A. R. Padhani, D.-M. Koh, and D. J. Collins, "Whole-Body Diffusion-weighted MR Imaging in Cancer: Current Status and Research Directions," *Radiology*, vol. 261, no. 3, pp. 700-718, 2011.
  [4] S. L. Giles et al., "Whole-Body Diffusion-weighted MR Imaging for Assessment of Treatment Response in Myeloma," *Radiology*, vol. 271, no. 3, pp. 785-794, 2014.
  [5] D. A. Hamstra, K. C. Lee, B. A. Moffat, T. L. Chenevert, A. Rehemtulla, and B. D. Ross, "Diffusion Magnetic Resonance Imaging: An Imaging Treatment Response Biomarker to Chemoradiotherapy in a Mouse Model of Squamous Cell Cancer of the Head and Neck," *Transl. Oncol.*, vol. 1, no. 4, pp. 187-194, 2008.
  [6] H. C. Thoeny and B. D. Ross, "Predicting and monitoring cancer treatment response with diffusion-weighted MRI," *Journal of Magnetic Resonance Imaging*, vol. 32, no. 1. pp. 2-16, 2010.
  [7] D. K. Hill et al., "Non-invasive prostate cancer characterization with diffusion-weighted MRI: Insight from in silico studies of a transgenic mouse model," *Front. Oncol.*, vol. 7, no. December, 2017.
  [8] L. Cheng et al., "Response evaluation in mesothelioma: Beyond RECIST," *Lung Cancer*, vol. 90, no. 3, 2015.
  [9] O. Ronneberger, P. Fischer, and T. Brox, "U-Net: Convolutional Networks for Biomedical Image Segmentation," *Miccai*, pp. 234-241, 2015.
  [10] K. He, X. Zhang, S. Ren, and J. Sun, "Delving deep into rectifiers: Surpassing human-level performance on imagenet classification," in *Proceedings of the IEEE International Conference on Computer Vision*, 2015, vol. 2015 International Conference on Computer Vision, ICCV 2015, pp. 1026-1034.
  [11] D. P. Kingma and J. L. Ba, "Adam: A method for stochastic gradient descent," *ICLR Int. Conf. Learn. Represent.*, pp. 1-15, 2015.
  [12] L. Zhang, L. Zhang, X. Mou, and D. Zhang, "A comprehensive evaluation of full reference image quality assessment algorithms," in *Proceedings—International Conference on Image Processing, ICIP*, 2012, pp. 1477-1480.
  [13] Z. Wang, A. C. Bovik, H. R. Sheikh, and E. P. Simoncelli, "Image quality assessment: From error visibility to structural similarity," *IEEE Trans. Image Process.*, vol. 13, no. 4, pp. 600-612, 2004.
  [14] H. Zhao, O. Gallo, I. Frosio, and J. Kautz, "Loss Functions for Image Restoration With Neural Networks," *IEEE Trans. Comput. Imaging*, vol. 3, no. 1, pp. 47-57, 2016.
  [15] R. Zhang, P. Isola, A. A. Efros, E. Shechtman, and O. Wang, "The Unreasonable Effectiveness of Deep Features as a Perceptual Metric," in *Proceedings of the IEEE Computer Society Conference on Computer Vision and Pattern Recognition*, 2018, pp. 586-595.
  [16] B. Zhu, J. Z. Liu, S. F. Cauley, B. R. Rosen, and M. S. Rosen, "Image reconstruction by domain-transform manifold learning," *Nature*, vol. 555, no. 7697, pp. 487-492, 2018.
  [17] B. Zhu, B. Bilgic, C. Liao, B. Rosen, and M. Rosen, "Deep learning MR reconstruction with automated transform by manifold approximation (AUTOMAP) in real-world acquisitions with imperfect training," in *Proc. Intl. Soc. Mag. Res. Med.*, 2018, p. 572.

APPENDIX

Understanding how Deep-Learning can Refine the Process of Spatial Smoothing in DWI 1. Background In this appendix, we explore how our deep-learned de-noising image filter (DNIF) is able to improve the perceived image quality in single average DWI acquisitions. In this study, we take a top-down approach to gain insight into how the DNIF filter works; we posit a number of hypotheses for how the DNIF filter (symbolised here through an operator $\tilde{H}$) processes a noisy input DWI image, f(x, y) to produce a filtered image, h(x, y):

$$\tilde{H}\{f(x,y)\} \to h(x,y) \quad (1)$$

Figure 7:
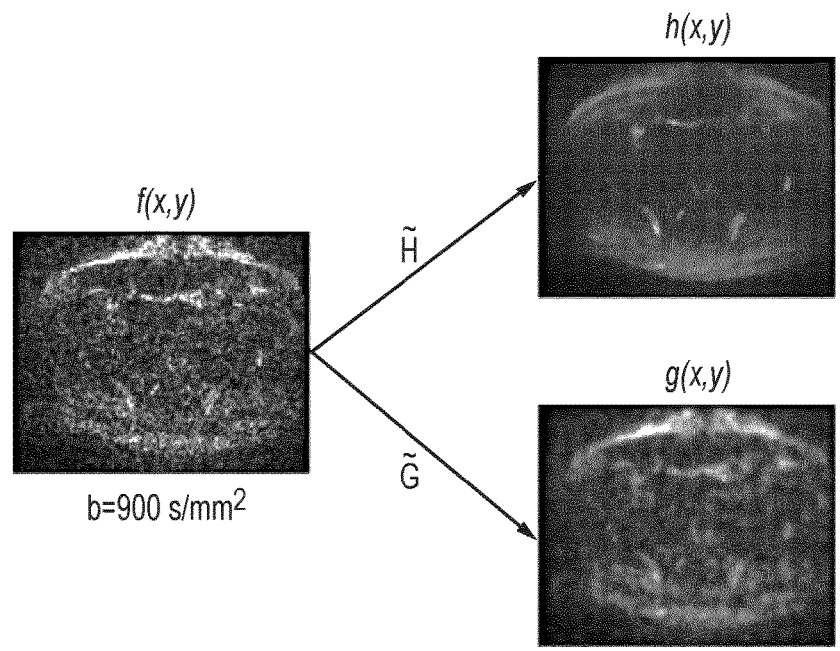
FIG. 7: Examples of our AI filter and smoothing filter $\tilde{G}$ operating on a low-quality single average image, f(x, y).

We perform in-silico simulation experiments to demonstrate evidence for our stated hypotheses, and compare results with a conventional Gaussian smoothing filter, $\tilde{G}$, which produces a smoothed image, g(x, y):

$$\tilde{G}\{f(x, y)\} = \frac{1}{\sqrt{2\pi\sigma^2}} \exp\left(-\frac{(x^2 + y^2)}{2\sigma^2}\right) \circledast f(x, y) \to g(x, y) \quad (2)$$

where $\circledast$ is the convolution parameter, and $\sigma^2$ is the smoothing variance (set to be $\sigma^2=4$ throughout these experiments). Examples of each of these smoothing processes applied to a noisy pelvic DWI image (NSA=1, b=900 s/mm2) are illustrated in FIG. 7.

2. Hypotheses

In the following we describe the hypotheses we make for how our DNIF filter is able to provide optimal smoothing of noisy DWI images. In each case, we state our hypothesis, explain the theory behind what our hypothesis represents in terms of image processing, and describe our experimental setup for how we validate our hypothesis. We illustrate our results and derive our conclusions accordingly.

2.1 DNIF is a Non-Linear Filter

We define non-linearity of the DNIF filter with respect to input image intensity as:

$$\tilde{H}\{a \cdot f(x,y)+b\} \ne a \cdot \tilde{H}\{f(x,y)\}+k, \forall a \in \mathbb{R}, k \in \mathbb{R} \quad (3)$$

Conversely it is well documented that is a linear filter, indicating that:

$$\tilde{G}\{a \cdot f(x,y)+k\} = a \cdot \tilde{G}\{f(x,y)\}+k$$

We demonstrate evidence for this hypothesis by synthesising a new image from the exemplar illustrated in FIG. 7 as f*(x, y)=f(x, y)+k, using a constant k=4, and attempt to recover the original DNIF-smoothed and Gaussian-smoothed images:

$$h^*(x,y)=\tilde{H}\{f(x,y)\}-k$$

$$g^*(x,y)=\tilde{G}\{f(x,y)\}-k$$

Figure 8:
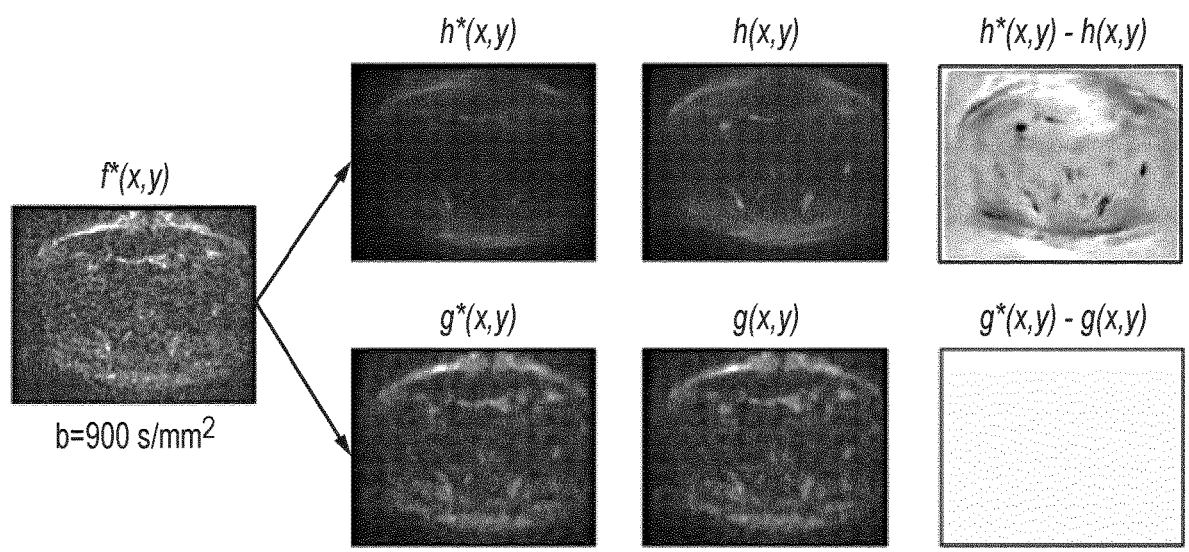
FIG. 8: Comparison of the non-linear properties of our deep-learning-based image smoothing filter with a conventional Gaussian smoothing filter. There is a clear difference between the recovered image h* and the original image h after the filter process indicating non-linearity of the filter.

Note that no value for scaling term a was included in this analysis as our deep-learning filter normalises images before image input making this term redundant. Maps of the differences between h and h*, and g and g* are shown in FIG. 8. It is evident that whilst the original Gaussian smoothed image g could be recovered from g*, the same was not true for the DNIF-filtered image h. This verifies our assumption of non-linearity for DNIF.

Figure 9:
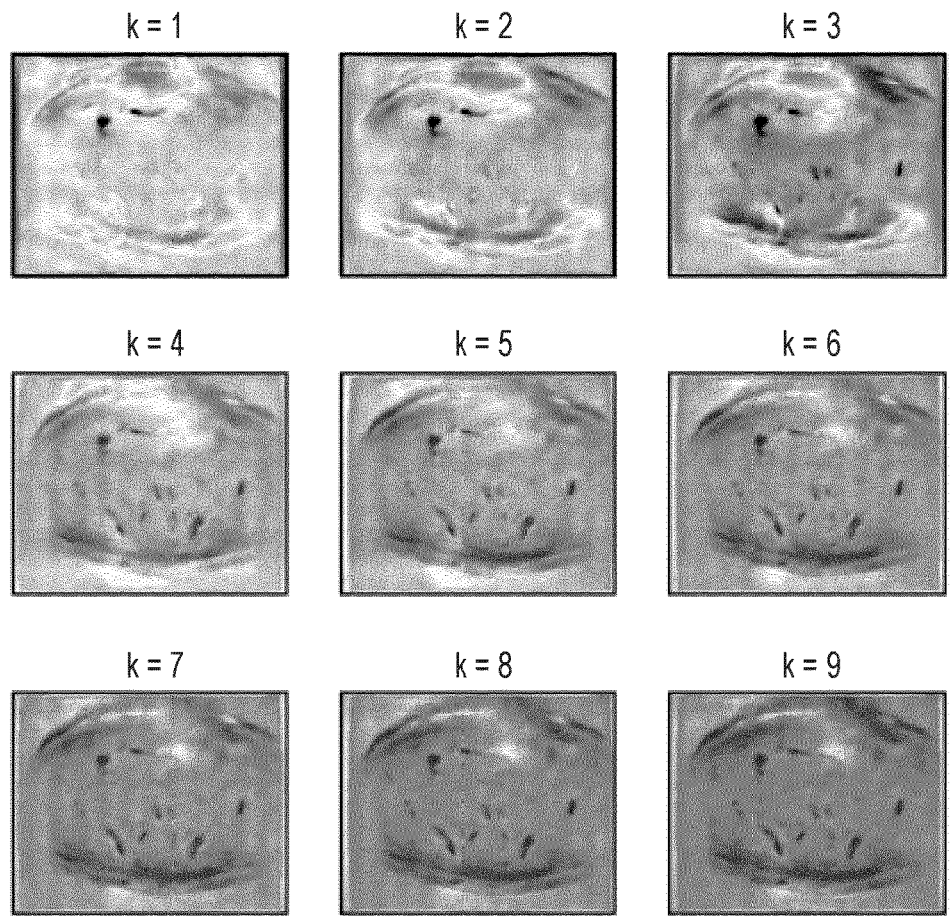
FIG. 9: Visual illustration of the degree of non-linearity observed by changing value of the bias term k.

In FIG. 9 we also demonstrate the effect of varying the magnitude of the bias term k for k∈{1, 2 ... 9}. It is clear that as k increases, the degree to which the deep-learning deviates from a linear filter worsens.

2.2 DNIF is a Spatially Variant Filter

Imaging filters that are spatially invariant (such as the Gaussian smoothing filter $\tilde{G}$) operate in the same manner on an image independently of whether there is a positional shift of the imaged object. We propose that DNIF is not spatially invariant so that the degree of smoothing within a certain region of the image is dependent on the position of that region within the entire imaging field. Mathematically, this can be described by firstly defining a new image f*(x, y)=f(x−$x_0$, y−$y_0$) that has been shifted by some amount $x_0$ (in the left-right direction) and $y_0$ (in the up-down direction). We propose that if DNIF is applied to image f* such that:

$$h^*(x,y)=\tilde{H}\{f(x,y)\}$$

then a reversal of this translation does not recover the original filtered pixel intensities:

$$h^*(x+x_0, y+y_0) \ne h(x,y)$$

Figure 10:
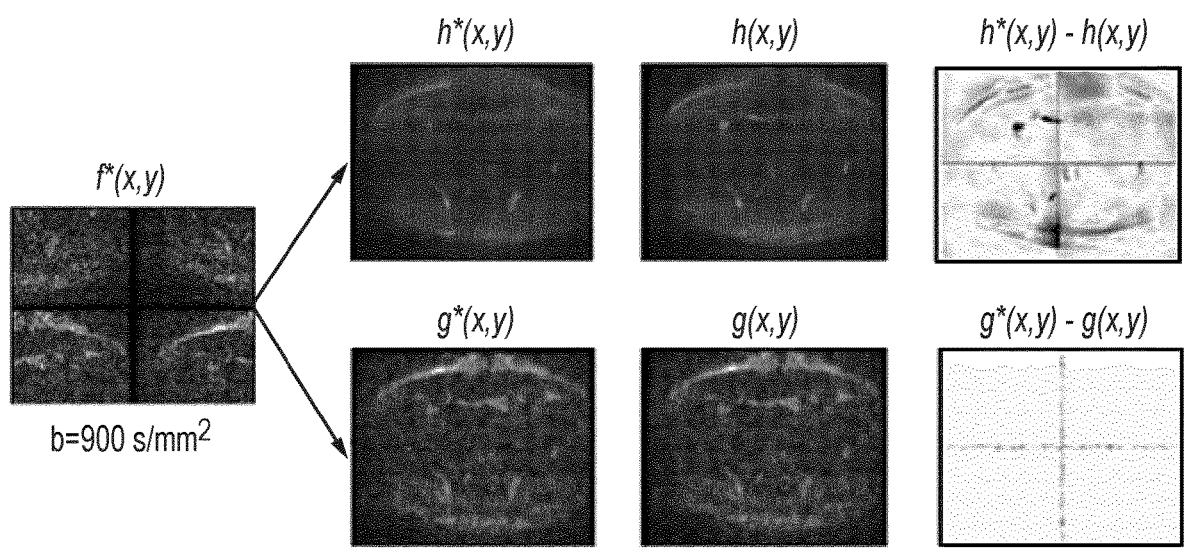
FIG. 10: Comparison of how shifting the input image prior to DNIF filtering can modify the final output pixel intensities. This confirms our hypothesis that this deep-learned filter is spatially variant compared with the spatially invariant Gaussian smoothing filter.

We validate this hypothesis by synthesising a shifted image f*(x, y) from an original image f(x, y) (same example demonstrated in hypothesis 2.1), and generating a new filtered image h*(x, y). We reverse the shift in the filtered image and compare pixel intensities with the original, unshifted filtered image h(x, y). This process is demonstrated in FIG. 10 for the case when the image is shifted by half of the imaging field-of-view in both directions, and is compared with a similar analysis for the Gaussian smoothing filter $\tilde{G}$. It is clear that whilst a shift in the image position has little effect on the output of $\tilde{G}$ (other than at the edges of the field-of-view), pixel intensities in the output of $\tilde{H}$ are modified as a result of the shift. This validates our hypothesis that DNIF is not a spatially invariant filter.

Figure 11:
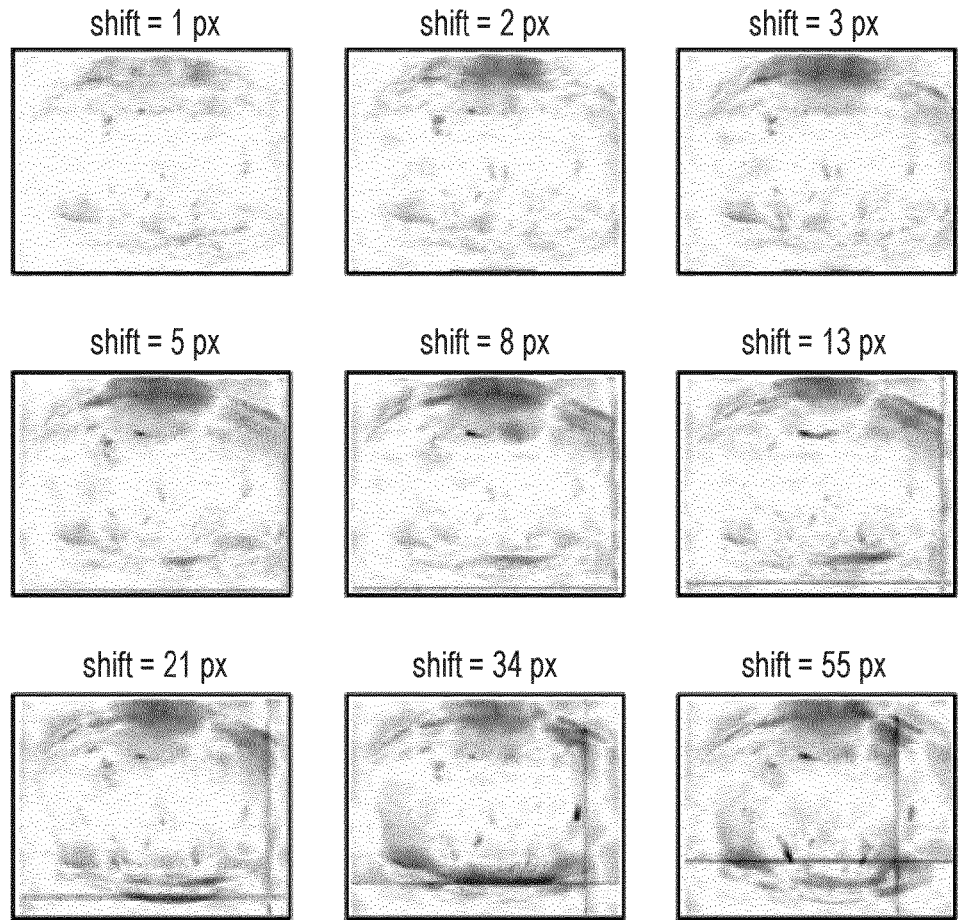
FIG. 11: Visual illustration of how varying the number of pixels the original image is shifted modifies the resultant filtered image.

To demonstrate the impact of the shifting magnitude on DNIF-filtered images, we performed the same experiment for $x_0=y_0 \in \{1, 2, 3, 5, 8, 13, 21, 34, 55\}$ pixels. Results for this experiment are illustrated in FIG. 11, where it is evident that as the magnitude of the shift increases, the degree to which the deep-learning deviates also increases.

2.3 DNIF is a Non-Local Filter

In the general sense, our definition of 'locality' for an arbitrary imaging filter, $\tilde{I}$, can be defined as $$\tilde{I}\{f(x,y)|x,y\}=\tilde{I}\{f(x,y)|\partial x, \partial y\}, \text{ where } \partial$$

$$x \subset x \text{ and } \partial y \subset y$$

That is, the image filter operating on an image f at location (x, y) is dependent only on the image intensities within some small neighbourhood ($\partial x$, $\partial y$) of the current location, with this neighbourhood being a small subset of the full image field-of-view (x, y). For conventional Gaussian smoothing filters the neighbourhood ($\partial x_g$, $\partial y_g$) is typically very small, and tuned via the smoothing variance $\sigma^2$ (Equation 2). Conversely, as the DNIF filter operates on the entire image field through a series of convolutional kernels that reduce the image field of view at each step, we expect that the neighbourhood of this filter ($\partial x_h$, $\partial y_h$) is much larger than for conventional approaches (if not dependent on the entire field of view):

$$(\partial x_g, \partial y_g) \in (\partial x_h, \partial y_h)$$

Figure 12:
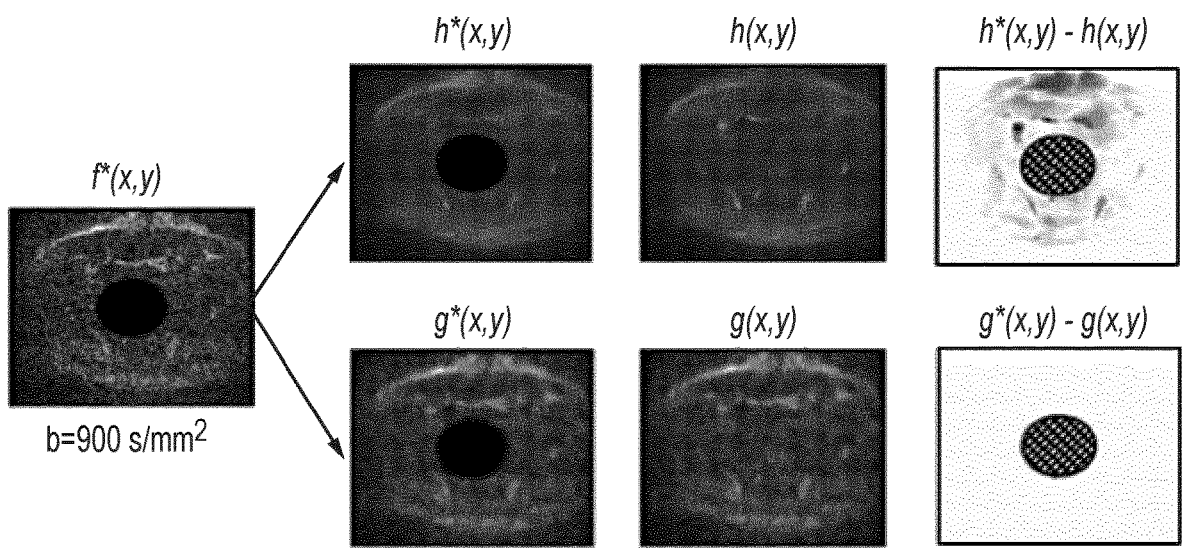
FIG. 12: Comparison of the locality properties of our deep-learning-based image smoothing filter with a conventional Gaussian smoothing filter. There is a clear difference between the recovered image h* and the original image h after the filter process indicating that changes occurring to portion of the image can affect pixel intensities throughout the rest of the image.
Figure 13:
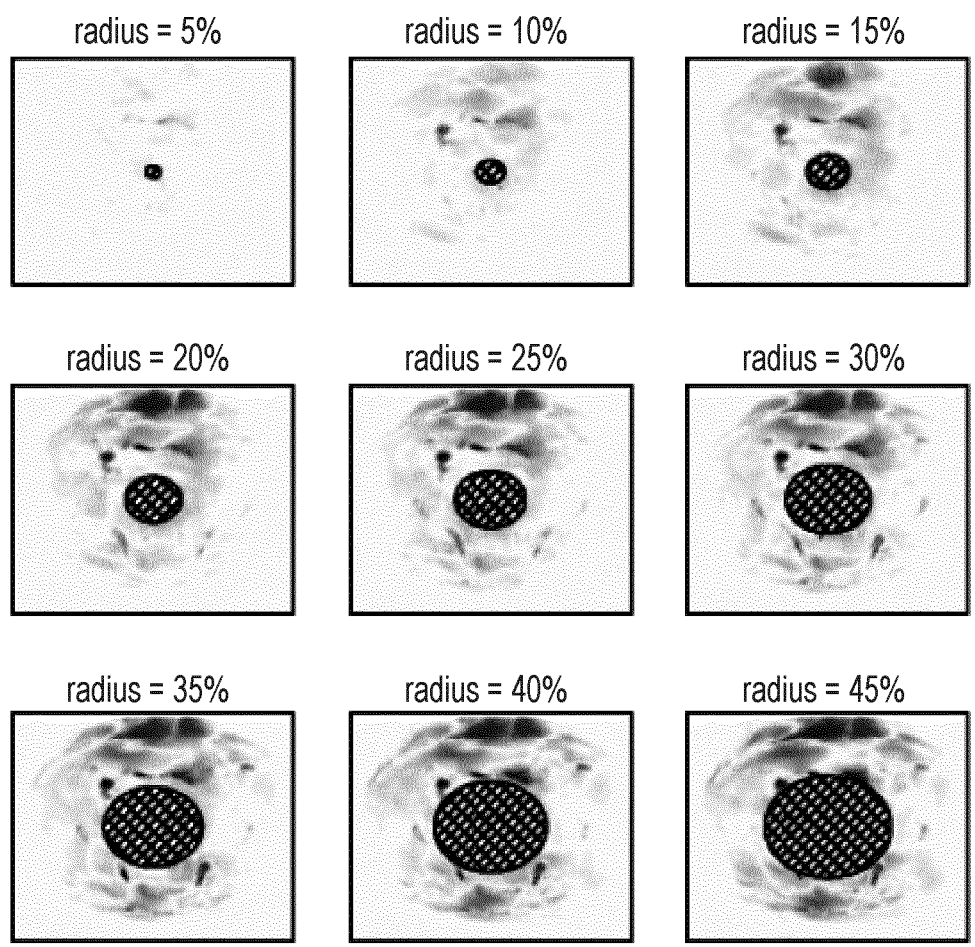
FIG. 13: Visual illustration of how increasing the area of removed pixels in the input image can increase the difference at other regions within the image once passed through the DNIF filter.

We provide evidence for this hypothesis by synthetically generating an input image f*(x, y) from an exemplar image f(x, y) for which pixels within a central circular region of the image have been set to zero (using the same exemplar image as for hypothesis 2.1). We derive a DNIF-filtered image, h*(x, y), and Gaussian-filtered image, g*(x, y), from the result. We compare the difference between these results and the filtered images obtained using the unmodified input images, as illustrated in FIG. 12. It is clear that modifying the pixel intensities in the central portion of the image has had considerable effect on the intensities edge of the field of view when using the DNIF filter, yet no such dependence is found for the Gaussian filter; this verifies our hypothesis on locality for H̃. In addition, we have tested the magnitude of change encountered for DNIF when varying the radius of the central circle (defined as the proportion of the image field of view). Results from this experiment (FIG. 13) indicate that values at the edge of the field-of-view are clearly changed when the radius is as low as 10%.

2.4 DNIF is an Edge-Preserving Filter

Figure 14:
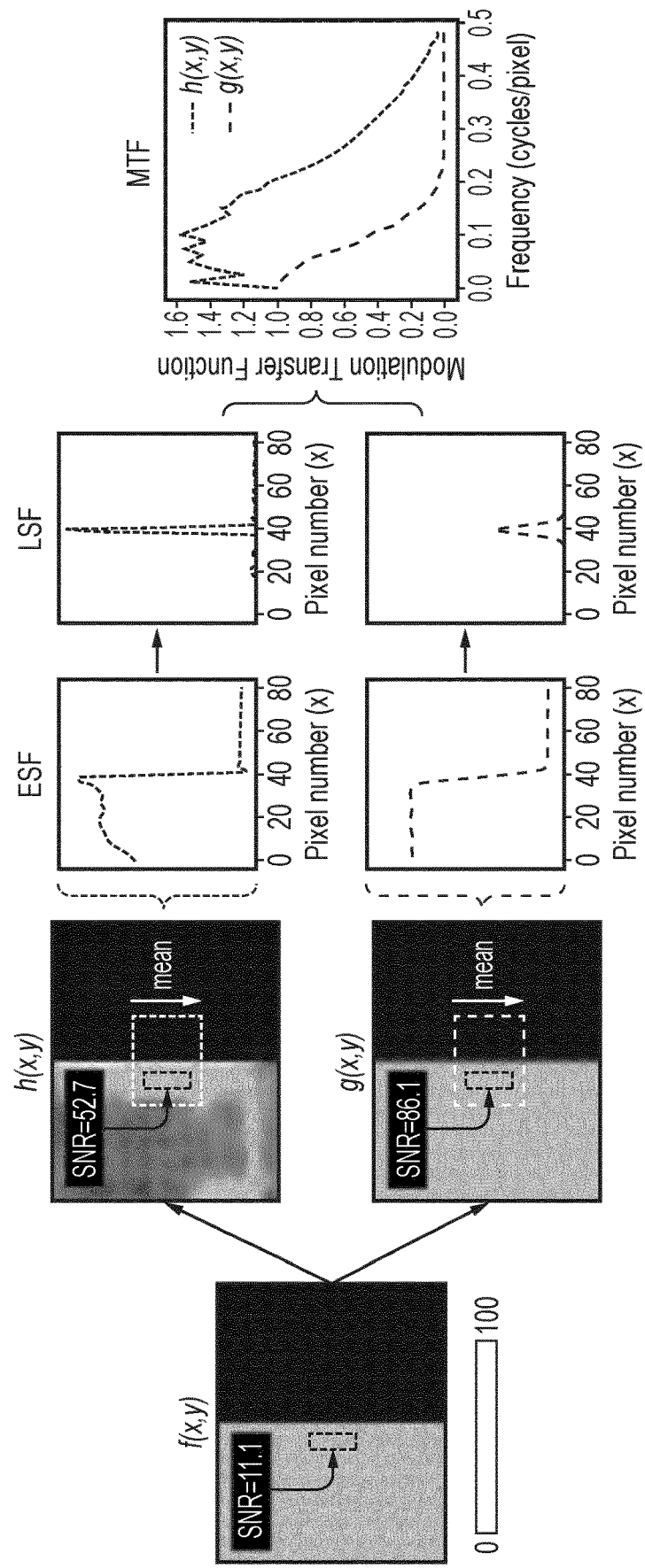
FIG. 14: An illustration of our experimental setup for verifying the hypothesis that DNIF is an edge-preserving smoothing filter. From left-to-right: The synthetic noisy knife-edge image, f, is passed through the DNIF and Gaussian filters to produces smoothed images h and g respectively. From these images, the edge-spread-function (ESF) is derived as the column-wise average of pixels within a bounding box of size 80×60 pixels (shown as dashed rectangles on the filtered images). The line-spread-function (LSF) is then derived as the first numerical derivative of the ESF, computed using the centered-difference formula. Finally, the modulation transfer function (MTF) is computed via the discrete Fourier transform of the LSF for each filter (normalised to the MTF value at zero frequency). We use the area under the MTF curve as a measure of filter performance, with higher area representing a better performing filter. It is clear from the MTF curves that the DNIF filter (upper curve) outperforms the Gaussian filter (lower curve) in this respect, from which we conclude that sharper edges can be resolved using DNIF.

We attribute some of the success of the DNIF filter due to its ability to preserve edges in the output filtered images. To demonstrate these edge-preserving qualities, we synthetically generated a noisy image containing a synthesised 'knife-edge' with uniform pixel intensities μ on the left half of the image, and zeros filling the right half. Rician distributed noise, with scale parameter σ, was added to this image. The signal-to-noise ratio (SNR) could be altered in these synthetic images by adjusting μ so that SNR=μ/σ, whilst we used a constant σ=6:99 in all experiments (this value was estimated from the background noise of an example singe-average DWI dataset). The synthetic knife-edge images were then passed through the DNIF and Gaussian filters in order to obtain estimates of the edge-spread-function (ESF), line-spread-function (LSF), and then modulation-transfer-function (MTF) for each filter; a full exposition of this experiment is illustrated in FIG. 14.

Figure 15:
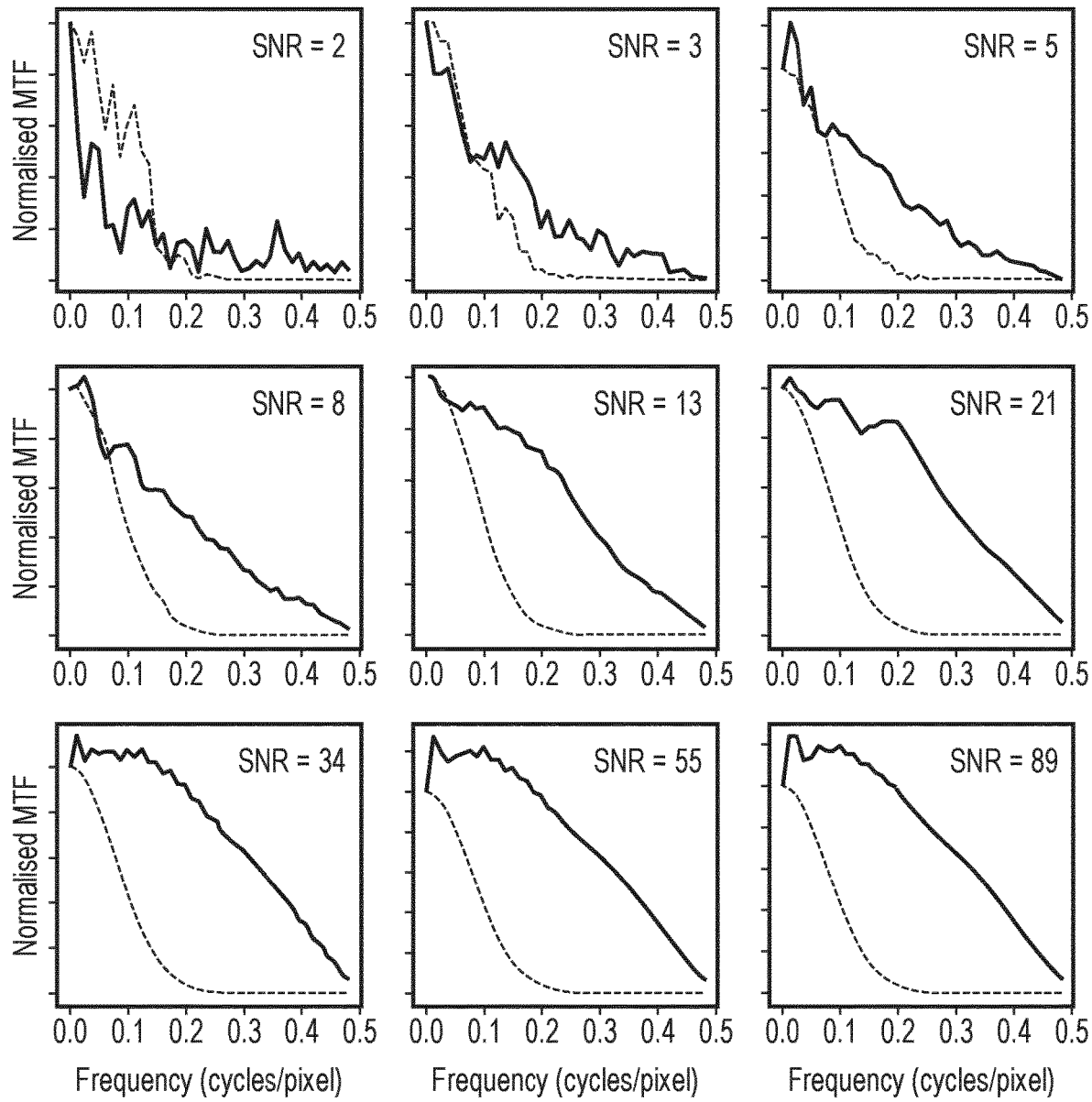
FIG. 15: Normalised modulation transfer functions (MTF) for the DNIF (solid line) and Gaussian (dashed line) smoothing filters, derived using synthetic knife-edge images with different signal-to-noise ratios (SNR). Our measure of filter performance is derived as the area under the normalised MTF curve. It is clear from these examples that the DNIF filter outperforms the Gaussian filter for SNR values of 3 or greater using these criteria.

The MTF is a well-known methodology for characterising the performance of an imaging system, and provides quantitative information of how well the imaging system is able to resolve structures over a range of spatial length scales and intensity contrasts. Here, we compare MTF curves generated by DNIF and Gaussian filters for different SNR values in the range SNRE∈ {2, 3, 5, 8, 13, 21, 34, 55, 89}. For each SNR, we simulated knife-edge image and measured the resultant the MTF 100 times, taking the average of these measurements to provide the final MTF for that SNR. Superior edge-preserving performance was identified as the filter that demonstrated the higher area under the normalised MTF curve. Results for these experiments are presented in FIG. 15, where we observe for SNR 3, the DNIF filter drastically outperforms the conventional smoothing filter. We therefore conclude that DNIF demonstrates improved edge-preserving properties over the Gaussian-smoothing filter.

3. Conclusions

Throughout this Appendix we have detailed our principle hypotheses into how our DNIF filter can produce optimal result for smoothing diffusion-weighted images with low SNR. We note that at present it is impractical to fully understand the complexities of how deep-learning methods make particular predictions given an input due to the thousands of parameters that are tuned during the training process. However, we have provided preliminary evidence that, in the very least, the DNIF filter is (i) non-linear, (ii) spatially variant, (iii) non-local, and (iv) edge-preserving. This demonstrates the true power for such methods, as generating 'hand-crafted' filters that can simultaneously achieve these properties is not practical, and so deep-learning methods are critical. Indeed, we posit from these results that the DNIF filter is learning complex relationships between pixels within the field-of-view based on their relative position and relative intensity. Moreover, we believe (due to spatial variance in particular) that the DNIF filter could be learning anatomical position in order to tune the degree of smoothing it performs at a particular location. Such properties imply that the DNIF filter should be used with caution, and potentially only used to process images acquired using certain diffusion-weighted sequences from which an initial cohort of training data has been obtained. To accelerate the training process and reduce the amount of new training data required for other diffusion-weighted sequences, transfer learning of our network could prove valuable.

The invention claimed is:

1. A method of performing diffusion-weighted magnetic resonance imaging, the method including a step of:
    using a neural network to filter a diffusion-weighted image of an object acquired by a magnetic resonance imaging scanner, the neural network being programmed to produce an output image from the acquired image;
    wherein the neural network improves a signal to noise ratio of the output image relative to the acquired image; and
    wherein the neural network, when applied to a synthetic knife-edge image to which Rician noise providing a signal-to-noise ratio of 13 or more is added, forms a curve of normalised values of modulation-transfer-function against frequency which has a higher area thereunder than an area under a corresponding curve of normalised values of modulation-transfer-function against frequency for a reference Gaussian smoothing filter, G̃:

$$\tilde{G}\{f(x, y)\} = \frac{1}{\sqrt{2\pi\sigma^2}} \exp\left\{-\frac{(x^2 + y^2)}{2\sigma^2}\right\} * f(x, y) \to g(x, y)$$

where f(x, y) is the noisy synthetic knife-edge image, g(x, y) is the filtered diffusion-weighted image, ⊛ is a convolution parameter, and $\sigma^2$ is a smoothing variance set such that $\sigma^2=4$.

2. The method according to claim 1 wherein the acquired image is acquired by the magnetic resonance imaging scanner at a given b-value and a given orientation for that b-value and without signal averaging.

3. The method according to claim 1 wherein the neural network is a spatially variant filter.

4. The method according to claim 1 wherein the neural network is a convolutional neural network.

5. The method according to claim 1, including a preliminary step of:
    acquiring the diffusion-weighted image using the magnetic resonance imaging scanner.

6. The method according to claim 1 wherein the acquired image is acquired at a first b-value and at given location in the object, and the method includes a further step of:
    combining the output image with one or more further diffusion-weighted images acquired at the given location in the object but at respective different b-values to derive an image of an apparent diffusion coefficient of water at the given location in the object.

7. The method according to claim 1 wherein the object is a human or animal subject.

8. The method according to claim 7, including a further step of:
    analysing the output image or an image derived therefrom for assessment of disease extent in the human or animal subject.

9. A computer program, stored on a non-transitory computer readable medium, that when executed, causes a computer to perform the method of claim 1.

10. An imaging system for performing diffusion-weighted magnetic resonance imaging, the system including:
- a magnetic resonance imaging scanner for acquiring a diffusion-weighted image of an object; and
- a computer system which receives the acquired image, and is programmed with a neural network which filters the acquired image to produce an output image from the acquired image;
- wherein the neural network improves a signal to noise ratio of the output image relative to the acquired image by a factor of X as measured by Y; and
- wherein the neural network, when applied to a synthetic knife-edge image to which Rician noise providing a signal-to-noise ratio of 13 or more is added, forms a curve of normalised values of modulation-transfer-function against frequency which has a higher area thereunder than an area under a corresponding curve of normalised values of modulation-transfer-function against frequency for a reference Gaussian smoothing filter, $\tilde{G}$:

$$\tilde{G}\{f(x, y)\} = \frac{1}{\sqrt{2\pi\sigma^2}} \exp\left\{-\frac{(x^2+y^2)}{2\sigma^2}\right\} \circledast f(x, y) \rightarrow g(x, y)$$

where f(x, y) is the noisy synthetic knife-edge image, g(x, y) is the filtered acquired image, $\circledast$ is a convolution parameter, and $\sigma^2$ is a smoothing variance set such that $\sigma^2=4$.

11. A computer system which receives a diffusion-weighted image of an object acquired by a magnetic resonance imaging scanner, and is programmed with a neural network which filters the acquired image to produce an output image from the acquired image;
- wherein the neural network improves a signal to noise ratio of the output image relative to the acquired image by a factor of X as measured by Y; and
- wherein the neural network, when applied to a synthetic knife-edge image to which Rician noise providing a signal-to-noise ratio of 13 or more is added, forms a curve of normalised values of modulation-transfer-function against frequency which has a higher area thereunder than an area under a corresponding curve of normalised values of modulation-transfer-function against frequency for a reference Gaussian smoothing filter, $\tilde{G}$:

$$\tilde{G}\{f(x, y)\} = \frac{1}{\sqrt{2\pi\sigma^2}} \exp\left\{-\frac{(x^2+y^2)}{2\sigma^2}\right\} \circledast f(x, y) \rightarrow g(x, y)$$

where f(x, y) is the noisy synthetic knife-edge image, g(x, y) is the filtered acquired image, $\circledast$ is a convolution parameter, and $\sigma^2$ is a smoothing variance set such that $\sigma^2=4$.

* * * * *